United States Patent [19]

Chang

[11] Patent Number: 4,849,173
[45] Date of Patent: Jul. 18, 1989

[54] EXCREMENT EXAMINATION UNIT

[76] Inventor: Mao-Kuei Chang, Floor 4, No. 28, Alley 1, Lane 131, Yen Chi Street, Taipei, Taiwan

[21] Appl. No.: 77,562

[22] Filed: Jul. 24, 1987

[51] Int. Cl.⁴ .................. G01N 1/48; G01N 33/72; A61B 5/00
[52] U.S. Cl. .......................... 422/56; 436/66; 422/101; 422/102; 422/58; 128/760; 128/638
[58] Field of Search ............... 436/66, 8; 422/56–61, 422/101, 102; 128/638, 749, 756, 759, 760

[56] References Cited

U.S. PATENT DOCUMENTS

| 3,539,300 | 11/1970 | Stone | 436/66 |
| 4,035,150 | 7/1977 | Jaffe | 436/66 |
| 4,159,193 | 6/1979 | Gauntley et al. | 422/58 |
| 4,235,839 | 11/1980 | Vesterberg | 422/58 |
| 4,562,043 | 12/1985 | Mennen et al. | 422/56 |
| 4,582,811 | 4/1986 | Pucci et al. | 436/66 |
| 4,645,743 | 2/1987 | Baker et al. | 422/58 |

Primary Examiner—Barry S. Richman
Assistant Examiner—T. J. Wallen

[57] ABSTRACT

An excrement examination unit includes a handle member having an elongate stirrer inserted in a housing. Fecal sample is picked up by the stirrer and dissolved into a medical saline solution by shaking the stirrer. Fecal solution is downwardly discharged and absorbed on a liquid-penetrable filter so that a simple occult blood test can be conducted by poking a test paper onto the filter through a slot formed in the housing to prevent a fecal contamination. Fecal solution is next downwardly discharged into a test tube for further laboratory examination.

1 Claim, 2 Drawing Sheets

EXCREMENT EXAMINATION UNIT

BACKGROUND OF THE INVENTION

A conventional method to detect a hemorrhage or parasites in a patient's feces is always performed by using a smear to pick up an excrement sample for its analysis. However, such a fecal processing may cause contamination or may emit an unpleasant odor to a laboratorian.

The present invention overcomes such drawbacks of a conventional fecal examination method.

SUMMARY OF THE INVENTION

The object of the present invention is to provide an excrement examination unit including a handle means having an elongate stirrer flexibly held and sealingly inserted in a housing. The stirrer may pick up a fecal sample to mix with a solution in the housing to conduct a preliminary test such as a detection of hemorrhage. A side slot formed on the housing prevents fecal contamination or a spread of unpleasant odor from the feces. A fecal solution is downwardly discharged through a bottom tube formed on a bottom portion of the housing into a test tube for further laboratory examination for parasites.

DETAILED DESCRIPTION

Figure 1:
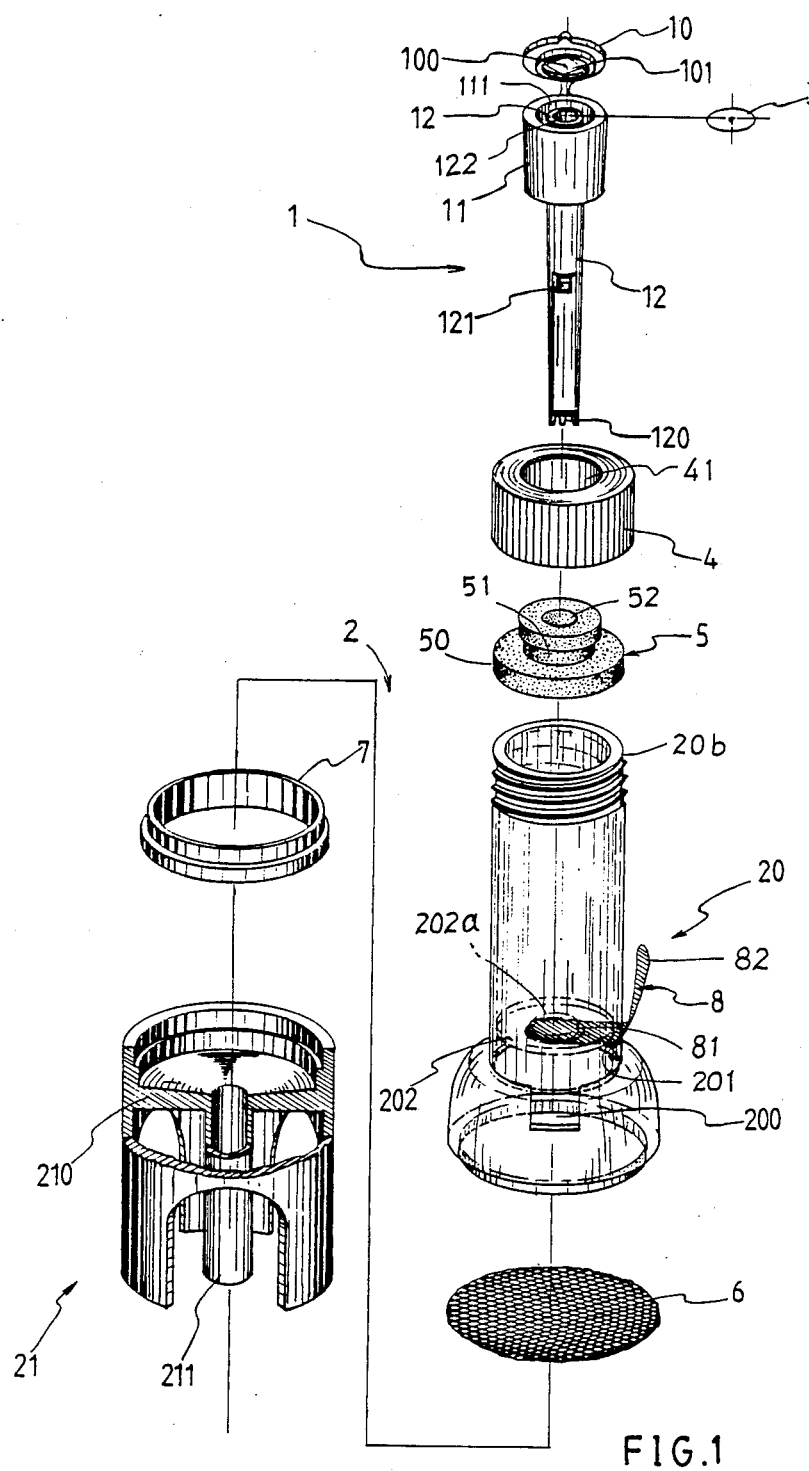
FIG. 1 is an exploded view showing all elements in construction of the present invention.
Figure 3:
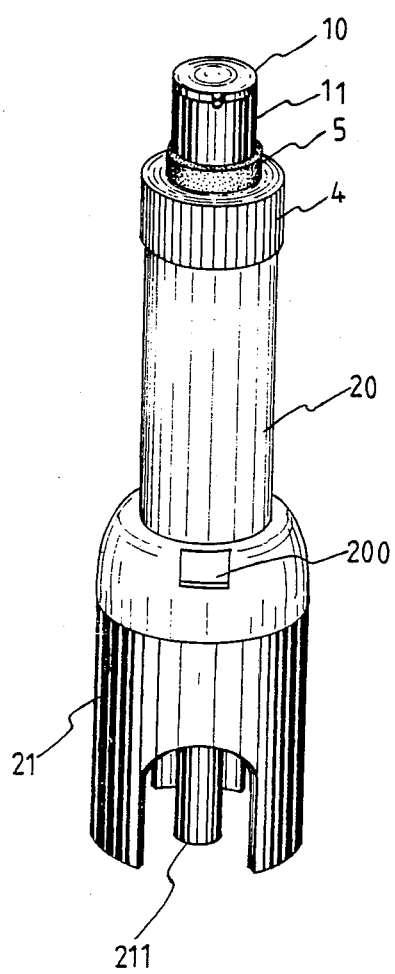
FIG. 3 is a perspective view of the present invention.
Figure 2:
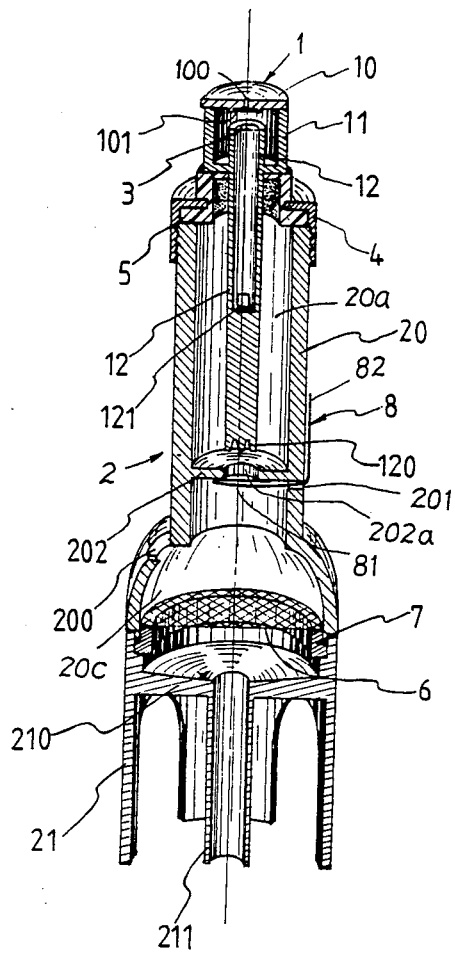
FIG. 2 is a sectional drawing of the present invention as assembled.

As shown in the figures, the present invention comprises: a handle means 1 and a housing 2.

The handle means 1 includes: a tubular handle portion 11 having a cavity 111 formed therein, an uppermost cover 10 removably formed on a top end of said tubular handle portion 11 and operatively sealing the cavity 111. A contrast test paper 101 is adhered on an inner surface of the cover 10 and has a-needle hole 100 drilled in a central portion of the cover 10. A hollow stem 12 connected to and positioned under the tubular handle 11 terminates with a stirring rake member 120 formed on the lowest end of the stem 12 and protrudes upwardly in the cavity 111 of tubular handle 11 to be sealed by a membrane 3 adhered on a top end of the stem 12 positioned under the cover 10. The hollow stem 12 is formed with at least a venting hole 121 through the stem 12. The contrast test paper 101 is adhered on the inner surface of the cover 10 to seal the hole 100. Upon a drilling by an external needle into the hole 100 to perforate the contrast test paper 101 and the membrane 3, the venting hole 121 is communicated with environmental air through the hollow stem 12, the perforated membrane 3, perforated test paper 101 and needle hole 100 formed in cover 10.

The housing 2 for encasing and supporting the handle means 1 includes: an upper hollow portion 20 and a lower base portion 21 positioned under the upper hollow portion 20, generally separated by a first partition plate 210 formed between the upper portion 20 and the lower portion 21.

The upper hollow portion 20 has a second partition plate 202 formed in a middle portion of the housing 2 above the first partition plate 210 defining an upper chamber 20a between the second partition plate 202 and a housing cap 4 secured on a top portion 20b of the upper portion 20. A lower chamber 20c is formed between the second partition plate 202 and the first partition plate 210.

The housing cap 4 has a central cap hole 41 and is removably secured to the upper hollow portion 20. Housing cap 4 is further packed by a packing member 5. The packing member 5 has a flange 50 secured between the cap 4 and the top portion 20b of the upper portion 20. An extension portion 51 protrudes upwardly through the cap hole 41 from the flange 50 and a stem hole 52 formed through the packing member 5 registers the hollow stem 12 into the hole 52 so that the stem 12 of the handle means 2 is held in the packing member 5 for operatively shaking the stirring rake member 120 within the upper chamber 20a. When securing the cap 4 on the upper portion 20 and holding the handle means 1 in the packing member 5, the rake member 120 is positioned proximately to the second partition plate 202.

The second partition plate 202 is formed with a drain hole 202a therethrough. A valve means 8 includes a water-proof sheet member 81 normally sealing the drain hole 202a and a tab portion 82 protruding outwardly from the sheet member 81 through a slit 201 laterally formed in a side wall of the upper portion 20 adjacent to the partition plate 202, whereby upon a withdrawal of the tab portion 82, the sheet member 81 is removed to open the drain hole 202a.

A filter means 6 held on a supporting ring 7 positioned above the first plate 210 is secured between the upper hollow portion 20 and the lower base portion 21. A rectangular slot 200 is formed in a side wall of the upper portion 20 between the two partition plates 202, and 210 proximate to the filter means 6. An actual test paper (not shown) is adhered on the filter means 6, which is made of liquid penetrable materials, through the slot 200.

A bottom tube 211 communicates with the lower chamber 20c and protrudes downwardly from the first partition plate 210 for connecting a test tube (not shown) thereunder. A bottom surface of the first plate 210 may be formed with several radial extensions (not shown) around the bottom tube 211 so as to allow the test tube to communicate with environmental air for a smooth discharge of liquid when connected under the bottom tube 211.

When using the present invention, the following procedures can be taken for excrement examination:

1. The cover 10 is opened to check whether the contrast test paper 101 is adhered inside the cover 10.

2. An external needle (not shown) is taken to perforate the test paper 101 and membrane 3 through the hole 100 for directing air into the chamber 20a for smooth discharge of a fecal solution.

3. An actual test paper (not shown) is adhered onto the filter means 6 by poking the paper through the rectangular slot 200.

4. The rake member 120 is used by a patient to pick up a small (0.5-1 gram) fecal sample to be kept within the upper chamber 20a.

5. A medical saline solution or other kind of solution is injected into the upper chamber by inserting an injecton syringe or a dispenser through the packing member 5.

6. By shaking the stem 12 and the stirring rake member 120, the fecal sample will be dissolved and dissipated into the saline solution in the upper chamber 20a.

7. The sheet member 81 of the valve means 8 is withdrawn to open the drain hole 202a to discharge the fecal solution downwardly into the lower chamber 20c, whereby the fecal solution is partially absorbed on the filter means 6 to penetrate the actual test paper adhered onto the filter means by its osmotic effect.

A few drops of identification reagent is dripped onto the actual test paper through the slot 200 to detect whether a hemorrhage phenomena (color change on test paper) is present in the fecal sample.

9. Drops of a reagent containing trace of blood are dripped onto the contrast test paper 101 as kept inside the cover 10 to detect a color change to check its performance for quality control.

10. The remaining fecal solution as filtered through the filter means 6 to remove residual materials in the fecal solution will be discharged through the bottom tube 211 to be received by a test tube (not shown), which is subject to a centrifugal sedimentation for further laboratory test such as a microscopic inspection for parasites.

The present invention has the following advantages over a conventional fecal examination as aforesaid:

1. The agitation, dissolving and processing of fecal sample is conducted within the sealed housing 1 to prevent unpleasant odor and contamination by a laboratorian.

2. A contrast test can be conducted to ensure the test precision and better quality control.

3. The fecal examination is done more conveniently and efficiently within such a compact unit.

4. The present invention can be easily handled or transported.

I claim:

1. An excrement examination unit comprising:

a handle means including a tubular handle portion having a cavity formed in said tubular handle portion, an uppermost removable cover formed on a top end of the tubular handle portion and operatively sealing the handle cavity and having a needle hole formed through said cover, a contrast test paper adhered on an inner surface of said cover sealable on said needle hole of said cover, a hollow stem connected to and positioned under said tubular handle portion having at least a venting hole formed in said stem, a stirring rake member connected on a lowest end of said stem, and a membrane adhered on a top end of said stem in said cavity, whereby upon a perforation by an external needle in said contrast test paper and said membrane through said needle hole of said cover, an air passage is formed through said hole of said cover, said perforated contrast test paper, said perforated membrane, and said venting hole of said hollow stem;

a housing for encasing and holding said handle means including an upper hollow portion, a lower base portion formed under said upper hollow portion, a first partition plate formed between said upper hollow portion and said lower base portion, a second partition plate formed in a middle position in said upper hollow portion above said first partition plate, said second partition plate including a drain hole, said lower base portion having a bottom tube protruding downwardly from said first partition plate, a rectangular slot formed in a side wall of said upper hollow portion between said second partition plate and said first partition plate, a housing cap sealingly secured to a top portion of said upper hollow portion and packed by a packing member, said packing member having a stem hole formed therein for inserting said hollow stem for holding said handle means in said housing;

a valve means having a water-proof sheet member normally sealing said drain hole of said second partition plate and a tab portion protruding outwardly from said sheet member through a slit laterally formed in said upper hollow portion adjacent to said second partition plate;

a filter means held on a supporting ring retained between said upper hollow portion and said lower base portion above said first partition plate, said filter means being liquid penetrable; and an actual test paper adhered on said filter means by poking through said rectangular slot, an upper chamber being defined between said second partition plate and said housing cap and a lower chamber defined between said second partition plate and said first partition plate, whereby upon an opening of the valve means to discharge a fecal solution which is made in said upper chamber by mixing a fecal sample kept on said rake member and a medical saline solution injected through said packing member into said lower chamber, the fecal solution as partially absorbed on said filter means will penetrate into said actual test paper for a preliminary test for a detection of a hemorrhage and a fecal solution is drained into a test tube connected under said bottom tube for further laboratory test of a microscopic inspection of parasites existing in the fecal sample.

* * * * *